(12) United States Patent
Boyde

(10) Patent No.: US 8,063,190 B2
(45) Date of Patent: Nov. 22, 2011

(54) NUCLEIC ACID-LINKED CONJUGATES AND METHODS FOR MAKING AND USING THEM

(76) Inventor: Tom Robin Caine Boyde, London (GB)

( * ) Notice: Subject to any disclaimer, the term of this patent is extended or adjusted under 35 U.S.C. 154(b) by 0 days.

(21) Appl. No.: 09/433,680

(22) Filed: Nov. 4, 1999

(65) Prior Publication Data
US 2004/0142323 A1 Jul. 22, 2004

(51) Int. Cl.
*C07H 21/02* (2006.01)
*C07K 1/00* (2006.01)
(52) U.S. Cl. ............... 536/23.1; 530/350; 530/402
(58) Field of Classification Search ............ 455/6, 91.1, 455/91.2; 536/23.1, 24.3, 24.31, 24.33
See application file for complete search history.

(56) References Cited

U.S. PATENT DOCUMENTS

| | | | | |
|---|---|---|---|---|
| 5,124,246 A | * | 6/1992 | Urdea et al. | 435/6 |
| 5,378,606 A | * | 1/1995 | Stern et al. | 435/6 |
| 5,391,723 A | * | 2/1995 | Priest | 536/23.1 |
| 5,474,895 A | * | 12/1995 | Ishii et al. | 435/6 |
| 5,516,635 A | * | 5/1996 | Ekins et al. | 435/6 |
| 5,656,731 A | * | 8/1997 | Urdea | 530/391.1 |
| 5,700,667 A | * | 12/1997 | Marble et al. | 435/91.3 |
| 5,718,915 A | * | 2/1998 | Virtanen et al. | 424/450 |
| 5,942,391 A | * | 8/1999 | Zhang et al. | 435/6 |
| 6,011,020 A | * | 1/2000 | Gold et al. | 514/44 |

FOREIGN PATENT DOCUMENTS

| | | | |
|---|---|---|---|
| EP | 453301 A2 | * | 4/1991 |
| WO | WO 9412216 A1 | * | 6/1994 |
| WO | WO 95/05480 | * | 2/1995 |
| WO | WO 95/35390 | * | 12/1995 |

OTHER PUBLICATIONS

Dunsworth-Browne et al (Nucleic Acids Research (1980) 8(3):543-554).*
Genbank Accession No. AY601635.*
Day et al (Biochem. J. (1991) 278:735-740).*
Niemeyer et al (Nucleic Acids Research (1994) 22(25):5530-5539).*
Genbank Accession No. AY601635; Feb. 7, 2006.*
Genbank Accession No. AY601635; Feb 7, 2006.*

* cited by examiner

*Primary Examiner* — Samuel Woolwine
(74) *Attorney, Agent, or Firm* — Kelly & Krause, L.P.; W. Dennis Drehkoff

(57) ABSTRACT

Compounds that are readily dissociable conjugates of a multiplicity of biologically active molecules are formed by bonding to each biologically active molecule one or more oligonucleotide chains selected to comprise partially complementary sequences that form duplexes with other such oligonucleotides attached to other biologically active molecules. The claimed conjugates and methods for preparing the conjugates of the invention can be used to link two or more biologically active molecules, as well as conjugating a multiplicity of biologically active molecules. In alternative embodiments, conjugates comprising such covalently linked oligonucleotides linked by one or a multiplicity of "bridging" oligonucleotides are provided. Methods for making these different types of conjugates and for using such conjugates for research, immunoassay, medical and technical applications are also provided by the invention. The disclosed methods provide for the formation of intermolecular links which are hydrophilic, of relatively low toxicity and antigenicity, are as flexible and extensible as desired, and are stable yet dissociable. Both the components and the conjugates of the invention can be isolated and purified with relative ease compared with other intermediates and conjugates.

6 Claims, No Drawings

NUCLEIC ACID-LINKED CONJUGATES AND METHODS FOR MAKING AND USING THEM

BACKGROUND OF THE INVENTION

1. Field of the Invention

The invention relates to non-covalent, readily dissociable conjugates between biologically active molecules. More particularly, the invention relates to such conjugates between biologically-active molecules using a flexible nucleic acid linking moiety that is covalently linked to each of the biologically-active molecules and that forms the conjugate by hybridization between the nucleic acid strands. Specifically, the invention relates to such conjugates wherein single-stranded nucleic acids are covalently linked to each of the biologically active molecules, and the conjugate is formed by hybridization of complementary segments of these single-stranded nucleic acids to one another or to a third, separate and distinct, single-stranded or partially single-stranded linking nucleic acid. Methods for making the conjugates of the invention are provided. Also provided are methods for using the conjugates of the invention in chemical or biochemical analysis, purification or manipulation of molecules for research or industrial purposes, or medical diagnosis or treatment.

2. Summary of the Related Art

In the biological and medical arts, it is frequently desirable to link together different molecules of the same or different type, for the performance of an assay or to embody the properties of each of a multiplicity of different molecules in the same conjugate molecule. It has become commonplace to covalently link together two protein molecules or a protein molecule with a non-protein molecule, so that the resulting combined molecule preserves at least some of the chemical properties of each of the original component molecules. Examples are the combination of an antibody molecule with an enzyme, or with a radioactive, or fluorescent, or electron-opaque molecule, so that the site where the antibody binds can be readily detected or the binding properties of the antibody can be more readily exploited for chemical assay of the substance bound by it. In other applications, for example, the antibody may be bound to a toxin, so that when the combined molecule is taken up by a target cell the latter may thereby be damaged or killed.

European Patent Application, Publication No. EP 0 134 127 A2 discloses polyamino acid-based linkers for conjugating proteins (such as antibodies and enzymes) and proteins to solid phases.

Although nucleic acids have been used in the past to interlink protein molecules, the methods employed have not fully exploited the advantages of nucleic acids as interlinking means: for example, the raw materials are readily available, and nucleic acids are of low intrinsic toxicity and antigenicity.

European Patent Application, Publication No. EP 0 154 884 A2 discloses nucleic acid-protein adducts comprising antibody molecules. The nucleic acid is derivatized with hapten, fluorescent or radioactive labels and covalently linked to *S. aureus* Protein A, and the resulting nucleic acid/antibody conjugates are used to amplify the signal provided by antibody/antigen binding.

International Patent Application, Publication No. WO91/17442 discloses nucleic acid-antibody hybrids comprising a bacteriophage promoter element operatively linked to a transcribed sequence, used to amplify and detect antibody binding to antigen.

European Patent Application, Publication No. EP 0 488 152 A2, discloses an immunoassay method wherein a detectable antibody-antigen complex is connected to a substrate by a double-stranded nucleic acid, which complex is released from the substrate by restriction endonuclease cleavage of the double-stranded nucleic acid.

European Patent Application, Publication No. EP 0 490 434 A1 discloses randomly-placed, multiply derivatized antibody molecules using nucleic acids and evidence that these adducts form duplexes with complementary, labelled nucleic acids.

International Patent Application, Publication No. WO 92/12164 discloses formation of three-dimensional nucleic acid structures for conjugation to proteins and other molecules.

Asseline et al., 1992, *Tetrahedron* 48: 1233-54 disclose nucleic acid-based heterobifunctional linkers.

Scouten and Konecny, 1992, *Analytical Biochemistry* 205: 313-8 disclose conjugation of antibodies with magnetic particles via duplex formation between oligo-A and oligo-T nucleic acid chains.

The art does not disclose a readily dissociable, nucleic acid-based linker for conjugating biologically active molecules. Such means have a number of uses. For example, molecules having binding specificities of varying affinity (such as antibodies) can be combined, permitting low-affinity molecules, especially those having great specificity, to be used in assays where their low affinity would otherwise preclude their use. Such linked antibody molecules are envisioned to be useful in improving the performance of immunoassay and competitive binding assays. Dissociable conjugation also permits linkage of targeting molecules (such as antibodies) and cytotoxic or other drugs, thereby improving drug delivery and specificity. In addition, the same or related cytotoxic drugs can be prepared with differing specificities (e.g., for a particular tumor type, targeted with a cell surface-specific targeting molecule); specific drugs could be prepared for an individual patient, based on expression of a particular cell-surface antigen. Finally, extremely high affinity and high selectivity binding conjugates can be made for chemical or biological purification by the combination of specific binding molecules recognizing, e.g., non-overlapping epitopes on a desirable analyte. Such selected and purified analytes can be released by dissociation of the complex, thereby reducing the affinity of binding overall and allowing the analyte to be recovered.

SUMMARY OF THE INVENTION

The invention provides nucleic acid-linked conjugates between biologically-active molecules.

In a first aspect, the invention provides a dissociable, non-covalent conjugate between a multiplicity of biologically-active molecules. In this aspect of the invention, each of the biologically-active molecules is linked to another by a flexible nucleic acid linker. In this aspect, a first single-stranded nucleic acid is covalently linked to a first biologically-active molecule, and a second single-stranded nucleic acid is covalently linked to a second biologically-active molecule. The conjugate is formed by hybridization to form a double-stranded heteroduplex that can be dissociated using, for example, heat or the addition of chaotropic agents to the conjugate or solutions thereof.

In this aspect of the invention, the flexibility of the nucleic acid linker is dependent on the length of the double-stranded heteroduplex (relative to the lengths of the single-stranded segments of the nucleic acid linker) and its complexity. Specifically, the flexibility of the nucleic acid linker varies inversely with the length of the double-stranded heteroduplex, and inversely with an increasing proportion of the linkage being double-stranded. In a preferred embodiment, the first nucleic acid comprises a first segment having a nucleotide sequence that is a homopolymeric sequence, and a second segment having a nucleotide sequence that is not a homopolymeric sequence, and is preferably a specific nucleotide sequence. The homopolymeric sequence is preferably a homopolymer of adenosine or deoxyadenosine (oligo(A) or oligo(dA)). In one embodiment, the first homopolymeric segment is covalently linked 5' to the second segment, and the nucleic acid is covalently linked to the first biologically active molecule at the 5' end of the nucleic acid. In another embodiment, the first segment is covalently linked 3' to the second segment, and the nucleic acid is covalently linked to the first biologically active molecule at the 3' end of the nucleic acid. Similarly, the second nucleic acid comprises a first segment having a nucleotide sequence that is a homopolymeric sequence, and a second segment having a nucleotide sequence that is not a homopolymeric sequence, and is preferably a specific nucleotide sequence. The homopolymeric segment of the nucleic acid is linked either 5' or 3' to the specific sequence and the biologically active molecule is linked to the end of the nucleic acid proximal to the homopolymeric sequence. The double-stranded heteroduplex is formed by hybridization (base-pairing) between the specific sequences of the first and second nucleic acids. The length of the double-stranded heteroduplex is dependent on the extent of the complementarity between these sequences in the two nucleic acids. The overall flexibility of the nucleic acid linkers of the invention is dependent on the absolute length of the double-stranded heteroduplex, and on the length of the heteroduplex in relation to the length of the single-stranded homopolymeric segment of each nucleic acid. The relationship between heteroduplex length and flexibility is generally inversely proportional for a constant percentage of double-strandedness; the relationship between flexibility and percent double-strandedness of the linker is also inversely proportional, due to the flexibility of single stranded nucleic acid.

Conjugates of the invention comprise one or a multiplicity of pairwise linkages of biologically-active molecules, wherein the biologically active molecules of each pair can be the same or different. In other preferred embodiments, each of the biologically-active molecules of the conjugates of the invention can be linked to a multiplicity of other biologically active molecules. In preferred embodiments, one of each pair of biologically active molecules comprising a multiplicity of conjugated biologically active molecules is an antibody or antigen-binding fragment thereof, an enzyme, a ligand for a receptor protein, or a drug. In other preferred embodiments, at least one of the conjugated molecules is a biologically-active molecule.

It is also an feature of this aspect of the invention wherein one of the covalently-linked nucleic acids of each complementary pair of nucleic acids comprises a homopolymeric sequence and a specifically hybridizing sequence, and its complement comprises a specifically hybridizing sequence.

In a second aspect of the invention is provided a dissociable, non-covalent conjugate between a multiplicity of biologically-active molecules, wherein each of the biologically-active molecules is linked to another by a flexible nucleic acid linker. In this aspect, the conjugate is formed by hybridization of a segment of a first single-stranded nucleic acid that is covalently linked to a first biologically-active molecule and a second single-stranded nucleic acid covalently linked to a second biologically-active molecule with a third nucleic acid, forming a double-stranded heteroduplex. In this aspect of the invention, the third "bridging" nucleic acid is, in one embodiment, a single-stranded nucleic acid. In another embodiment, the third nucleic acid comprises an overlapping array of partially-complementary nucleic acids, wherein the ends of the array comprise a single-stranded nucleic acid complementary to the first or second single-stranded nucleic acid of the conjugate. In this aspect, each of a multiplicity of single-stranded and partially complementary nucleic acids form a concatenated hybrid of alternating segments of double-stranded or partially double-stranded heteroduplex. At either end of this concatenate is a single-stranded segment complementary to a segment of either the first or second nucleic acid covalently linked to a biologically-active molecule. Formation of a double-stranded duplex between the ends of the concatenate and each of the covalently linked nucleic acids completes formation of the linked conjugate. The degree of dissociability of the conjugate in embodiments of this aspect of the invention is dependent on the strength of the duplex having the lowest degree of complementarity, the shortest length, and/or the highest A-T content.

In preferred embodiments, the first nucleic acid covalently attached to a biologically active molecule comprises a first homopolymeric sequence, and a second sequence that is preferably a specific nucleotide sequence. The homopolymeric sequence is preferably a homopolymer of adenosine or deoxyadenosine (oligo(A) or oligo(dA)). In one embodiment, the first homopolymeric segment is covalently linked 5' to the second segment, and the nucleic acid is covalently linked to the first biologically active molecule at the 5' end of the nucleic acid. In another embodiment, the first segment is covalently linked 3' to the second segment, and the nucleic acid is covalently linked to the first biologically active molecule at the 3' end of the nucleic acid. Similarly, the second nucleic acid covalently linked to a biologically active molecule comprises a first nucleotide sequence that is a homopolymeric sequence, and a second nucleotide sequence that is preferably a specific nucleotide sequence. The homopolymeric segment of the nucleic acid is linked either 5' or 3' to the specific sequence and the biologically active molecule is linked to the end of the nucleic acid proximal to the homopolymeric sequence. In this embodiment, the directionality of the nucleic acid comprising each of the ends of the nucleic linker array determines the end (5' or 3') of each of the nucleic acids covalently linked to a biologically-active molecule, providing for annealing and hybridization between the covalently linked nucleic acids and the nucleic acid linker. The double-stranded linker is formed by hybridization between specific sequences of each of the first and second nucleic acids and with the nucleic acid linker. In this aspect, the length of the double-stranded heteroduplex is dependent on the extent of the complementarity between the sequences of the component nucleic acids, and it will be understood that the linker optionally comprises alternate segments of single-stranded and double-stranded nucleic acid. In this embodiment, the overall flexibility of the nucleic acid linkers of the invention is dependent on the absolute length of the double-stranded heteroduplex, and on the total length of the heteroduplex region in relation to the length of the single-stranded homopolymeric segment of each covalently-linked nucleic acid. The relationship between heteroduplex length and flexibility is generally inversely proportional for constant percentage double-strandedness; the relationship between flexibility and percent double-strandedness of the linker is also inversely proportional.

Conjugates of the invention comprise one or a multiplicity of pairwise linkages of biologically-active molecules, wherein the biologically active molecules of each pair can be the same or different. In other preferred embodiments, each of the biologically-active molecules of the conjugates of the invention can be linked to a multiplicity of other biologically active molecules. In preferred embodiments, one of the pair of biologically active molecules is an antibody or antigen-binding fragment thereof, an enzyme, a ligand for a receptor protein, or a drug. In other preferred embodiments, at least one of the conjugated molecules is a biologically-active molecule.

It is also an feature of this aspect of the invention wherein one of the covalently-linked nucleic acids of each complementary pair of nucleic acids comprises a homopolymeric sequence and a specifically hybridizing sequence, and its complement comprises a specifically hybridizing sequence.

In a third aspect of the invention, methods of preparing each of the embodiments of the invention disclosed herein are provided. The invention provides a method of making a dissociable, non-covalent conjugate between a multiplicity of biologically-active molecules, wherein each of the biologically-active molecules is linked to at least one other by a nucleic acid linker that can be a flexible linker. The method comprises the steps of:
 (a) covalently linking a first single-stranded nucleic acid to a first biologically active molecule;
 (b) covalently linking a second single-stranded nucleic acid to a second biological molecule, wherein a segment of the first and second nucleic acids are complementary and capable of forming a double-stranded heteroduplex by hybridization of the complementary segments;
 (c) contacting the nucleic acid-linked first biologically active molecule of step (a) with the nucleic acid-linked second biologically active molecule of step (b) for a time and at a temperature and cation concentration wherein a heteroduplex is formed between the complementary segments of the nucleic acids. For preparing conjugates comprising a multiplicity of biologically active molecules, steps (a) or (b) can be conducted wherein a one or a multiplicity of nucleic acids are covalently linked to a biologically-active molecule.

Also provided by the invention is a method for preparing a dissociable, non-covalent conjugate between a multiplicity of biologically-active molecules, wherein each of the biologically-active molecules is linked to at least one other by a nucleic acid linker that can be a flexible linker, the method comprising the steps of:
 (a) covalently linking a first single-stranded nucleic acid to a first biologically active molecule;
 (b) covalently linking a second single-stranded nucleic acid to a second biological molecule, wherein a segment of the first and second nucleic acids are complementary to a third nucleic acid and capable of forming double-stranded heteroduplexes by hybridization of the complementary segments;
 (c) contacting the nucleic acid-linked first biologically active molecule of step (a) and the nucleic acid-linked second biologically active molecule of step (b) with the third nucleic acid of step (b) for a time and at a temperature and cation concentration wherein a heteroduplex is formed between the complementary segments of the nucleic acids.

For preparing conjugates comprising a multiplicity of biologically active molecules, steps (a) or (b) can be conducted wherein a one or multiplicity of nucleic acids are covalently linked to a biologically-active molecule. The third "bridging" nucleic acid is, in one embodiment, a single-stranded nucleic acid. In another embodiment, the third nucleic acid comprises an overlapping array of partially-complementary nucleic acids, wherein the ends of the array comprises single-stranded nucleic acids complementary to the first or second covalently-linked single-stranded nucleic acids of the conjugate.

It is a particular aspect of the conjugates and methods of this invention that covalent adducts formed between biologically-active molecules and nucleic acids can be formed at a specific site within both the nucleic acid and the biologically-active molecule. Preferably the linkage is located in each nucleic acid at the 5' or 3' end of the nucleic acid chain, most preferably wherein the linkage is derived from or attached to the nucleic acid backbone, particularly at a sugar residue. The specific site of covalent attachment in the biologically-active molecule depends in large part on the structure of the molecule and is limited to the types of covalent attachments that do not destroy biological or other activity. An example of one type of preferred linkage is linkage through sulfhydryl groups, preferably formed by reduction of disulfide bonds, linked to maleimides. Another example are hydrazide linkages made with derivatized —S—$(CH_2)$—COOH groups using, for example, iodoacetic acid.

It is one advantage of the conjugates of this invention that the nucleic acid linker provides a dissociable linkage between the conjugated biological molecules. As set forth above, the conjugates of the invention are held together by hybridization of segments of single-stranded nucleic acids to form double-stranded heteroduplexes. These heteroduplexes can be dissociated, and the conjugate cleaved, using, for example, heat or the addition of chaotropic agents. Upon dissolution, the biologically-active molecules can be separated and analyzed individually, or one of the molecules can be removed by differential precipitation, affinity column chromatography, and other separation means well-known in the art. The conjugate linkage is stable, however, in the absence of the addition of heat or chaotropic agents to the conjugate or solutions thereof.

It is another advantage of this invention that the strength and flexibility of the linkage is continuously variable by the use of nucleic acids forming different lengths of double-stranded heteroduplex, and by varying the percentage of the linker that is double-stranded. Double-stranded nucleic acid is well-understood to form a more rigid structure (termed a "rigid rod") than single-stranded nucleic acid, which approximates a random coil conformation. Thus, the rigidity of the linkage is advantageously adjusted by either the absolute length of the double-stranded heteroduplex formed, or this length relative to the single-stranded homopolymer segment of each covalently linked nucleic acid. In addition, the strength of the linkage, as measured by either the amount of heat required for denaturating the double-stranded heteroduplex (reflected in the melting temperature, $T_m$) or the concentration of chaotropic agent required to dissociate the duplex, depends on the length and complexity of the heteroduplex (see *Nucleic Acid Hybridization: A Practical Approach*, Hames and Higgins, ed., IRL Press: Oxford, UK (1985) for a more detailed discussion of nucleic acid hybridization behavior). Variation in both the absolute length of the heteroduplex, the relative length of the heteroduplex in relation to the single-stranded homopolymeric segment and the complexity of the hybridization provide variable degrees of linker strength and flexibility.

It is specifically an advantage of this invention that nucleic acids are used as linking means. Although nucleic acids have been used in the past to interlink protein molecules (as described above in the Background of the Invention), the methods employed have not been used to fully exploit the potential advantages of nucleic acids as interlinking means.

These advantages include the ready availability of nucleic acids, including isolation from natural sources; synthesis including automated synthesis; and the existence of nucleic acid analogues at the base, backbone and intrastrand linking levels. Such nucleic acid analogues may have desirable properties, such as resistance to enzymatic attack. In addition, nucleic acids are of low intrinsic toxicity and low antigenicity. Nucleic acids are particularly appropriate for the methods and compositions of the instant invention, because the linkage between molecules can be extended to a considerable length, while remaining flexible. Flexibility as desired can be achieved by arranging that a sufficient length of one or more of the chains used is (or are) single-stranded. Another advantage of nucleic acid linkers as provided by the instant invention is that very high degrees of purity of the component molecules can be attained. The use of nucleic acid basepairing provides a high degree of specificity of association, allowing a multiplicity of different combinations of biologically active molecules to be interlinked at specific sites covalently linked to complementary nucleic acids. The strength and thermodynamic stability of the double-stranded link can also be varied by the length and degree of complexity of the heteroduplex segment of the nucleic acid linker, while these heteroduplexes remain completely dissociable under relatively mild conditions, in contrast to covalent linking means known in the art. Association, dissociation and re-association are in favorable cases reversible and reproducible, permitting the same or different combinations of the linked biologically active molecules to be produced. Finally, it is an advantage of the methods and compositions of this invention that a multiplicity of biologically active molecules can be linked, providing synthetic flexibility in preparing different combinations of biologically active molecules.

Methods of use and uses for the conjugates of the invention are also provided. In a preferred embodiment, medical uses of the conjugates of the invention are provided. These uses include specific targeting of cytotoxic and other drugs, in cancer chemotherapy and other instances of therapeutic removal of certain cells from a mammalian body (for example, with virus-infected cells). In preferred embodiments of this aspect of the uses of the conjugates of the invention are provided specific delivery means for drug delivery. Also preferred are embodiments whereby a combination of a multiplicity of cytotoxic or other therapeutically useful molecules are conjugated to one or a multiplicity of targeting molecules. The conjugates of the invention are also provided for diagnostic uses, including the specifically delivery and localization of detectable labels at pathologic sites in vivo.

Also provided are analytical uses for the conjugates of the invention. Examples of this aspect of the invention are reagents for enzyme-linked immunosorbent (ELISA) assay.

Specific preferred embodiments of the present invention will become evident from the following more detailed description of certain preferred embodiments and the claims.

DETAILED DESCRIPTION OF THE PREFERRED EMBODIMENT

The invention relates to dissociable conjugates of biologically active molecules and methods for preparing and using such conjugates.

One essential technical feature of this invention are methods of linking two biologically active molecules, such as two protein molecules, or a protein molecule with one or more other molecules which may themselves be protein molecules or other kinds of molecules in any combination. Such conjugates are formed wherein said molecules are linked in a conjugate using two or more oligonucleotide chains, by attachment of each biologically active molecule to one or more oligonucleotides, wherein the desired conjugate molecule is allowed to form by a process of complementary base-pairing between a suitably-designed sequence of each oligonucleotide with a suitably-designed complementary sequence of at least one other oligonucleotide. Thus typically a biologically active molecule is joined to another biologically active molecule through a greater or lesser length of single nucleic acid strand, then a duplex, then another single strand. Methods are also included in which a third oligonucleotide, distinct from the covalently linked oligonucleotides, being free from covalent attachment to any biologically active molecule, is used as a "bridging" oligonucleotide and forms a heteroduplex with a covalently linked oligonucleotide. Alternative embodiments of the bridging oligonucleotide comprise an array of partially-complimentary oligonucleotides that form an intermittently double-stranded bridging concatenate, having a single stranded segment at either end of the bridging oligonucleotide concatenate, complementary to either one or the other or both of the covalently linked oligonucleotides. Embodiments are also provided where two biologically active molecules are covalently linked to either end of an oligonucleotide, and a dissociable conjugate is provided wherein a one or a multiplicity of oligonucleotide-linked biologically active molecules are dissociably conjugated thereby.

One advantage to be obtained by the use of the methods of the invention is that the combined molecules can be produced under unusually mild, non-damaging conditions, in high yield and purity, and having an unusually long and in appropriate cases an unusually flexible link. In many cases, length and/or flexibility of the link are advantageous properties of the conjugates of the invention.

For the purposes of this invention, the term "nucleic acid" is intended to encompass RNA, DNA and hybrids and mixtures thereof. It will be understood by those with skill in the art that certain combinations of nucleic acids and derivatization/chemical coupling methods are inappropriate (e.g., RNA is generally inappropriate for use with periodate, due to its susceptibility to degradation). Those with skill in the art will recognize other inappropriate combinations and select the chemical conjugation method with the chemical stability and compatibility of the nucleic acid in mind. Nucleic acids of this invention also include modified bases (such as xanthine, hypoxanthine, inosine, azaguanine, and bromouridine), modified sugars (dideoxyribose, and 3' deoxyribose) and modified linkages (phosphorothioate, alkyl phosphotriester, methylphosphonate and phosphoramidates). Also intended to fall within the scope of this invention are hybrid molecules known in the art as "protein nucleic acids," i.e., wherein the sugar/phosphate backbone structure of the nucleic acid is replaced with a peptide/amino acid based structure. (See *Antisense Research and Applications*, Crooke and Lebleu, eds, CRC Press: Boca Raton, Fla., 1993, incorporated by reference in its entirety for a more detailed discussion of nucleic acid analogues).

For the purposes of this invention, the term "biologically active molecules" is intended to encompass any molecule having any biologically-relevant effect, including particularly macromolecules. Also included in this definition are molecules exhibiting a binding specificity or affinity characteristic of a biological molecule, i.e., having a binding affinity greater than $10^{-6}$ M. Specifically encompassed within this definition are antibodies and antigen-binding fragments thereof, enzymes, proteins including receptor proteins and ligand binding fragments thereof, ligands, antigens, haptens, detectably-labeled molecules, including fluorescent, radio-isotope and affinity-labeled molecules, synthetic binding molecules, and drugs including cytotoxic drugs.

For the purposes of this invention, the term "heteroduplex" is intended to mean a double-stranded segment of a nucleic acid derived from separate oligonucleotides. Particularly encompassed by the definition are duplexes comprised of oligonucleotides covalently linked to biologically active molecules. Also particularly encompassed by this definition are duplexes formed using a "bridging" oligonucleotide or concatenated linker as described herein.

For the purposes of this invention, a "concatenate" or "concatenated linker" is intended to encompass a linker comprised of a multiplicity of partially complementary oligonucleotides linked by hybridization to form an intermittently double-stranded duplex having a single-stranded segment at each end, to provide for hybridization to covalently linked nucleic acids.

For the purposes of this invention, the term "hybridization" is intended to encompass the formation of double-stranded duplex regions in a nucleic acid, formed by annealing and basepair formation between nucleic acids in antiparallel fashion. Generally, the term is intended to have the meaning understood by those with skill in the art, for example, in Sambrook et al. (1990, *Molecular Cloning: A Laboratory Manual*, 2d ed., Cold Spring Harbor Laboratory Press: New York).

The oligonucleotides and other nucleic acid components of the present invention are advantageously prepared by genetic engineering means, chemical or enzymatic digestion, enzymatic assembly, chemical synthesis, or combination thereof. Most preferably, nucleic acids are prepared by solid phase chemical synthesis.

Oligonucleotides are conjugated to biologically active molecules by derivatization of either the oligonucleotide or the biologically active molecule or both. Oligonucleotides preferably comprise a terminal ribose residue, prepared either during synthesis or added enzymatically, for example, using terminal transferase. Covalent adducts are prepared using chemical crosslinking methods well known in the art, most preferably by reaction of carbohydrazide derivatives or an amine with a dialdehyde. Maleimido groups can be used to conjugate oligonucleotides to sulfhydryls groups derived, for example, from a protein. Covalent adducts between nucleic acid and biologically active molecules such as proteins are prepared whereby the ratio of oligonucleotide to protein ranges is preferably about 1; also preferred are preparations providing a biologically active molecule covalently linked to one or a multiplicity of oligonucleotides.

Conjugates of the invention are typically formed simply by allowing the covalent oligonucleotide-protein adducts or other biologically active molecule adducts to be in contact in solution at a temperature, a concentration and a cation concentration appropriate for heteroduplex formation. Exact conditions of hybridization will vary according to well-established principles well known to those with skill in the art. (See *Nucleic Acid Hybridization: A Practical Approach*, ibid.)

Similarly, the conditions necessary to dissociate the conjugates of the invention are chosen based on the nature of the biologically active molecule and the strength and complexity of the heteroduplex forming the conjugated linkage. Conditions useful for dissociating heteroduplex linkages include increasing the temperature of the solution to above the $T_m$ of the heteroduplex (at a temperature that does not denature or otherwise compromise the stability or biological activity of the covalently-linked biologically-active molecules); reducing the monovalent or divalent cation concentration (such as sodium ions or magnesium ions); and adding chaotropic agents such as formamide, guanidinium hydrochloride or guanidinium isothiocyanate to a concentration sufficient to disrupt heteroduplex basepairing; and combinations of such techniques and conditions. Specific methods for causing heteroduplex dissociation are well-known in the art.

Regarding the homopolymeric segments of the nucleic acids of the invention, polyadenylic acid (polyA) is preferred. In preparing the conjugates of the invention, it is preferable not to prepare combinations of nucleic acids whereby the homopolymeric sequences are complementary (e.g., polyA with polyythymidylic (polyT) or polyuridylic (polyU) homopolymers or polycytidylic (polyC) with polyguanidylic (polyG) homopolymers). Deoxyribonucleic homopolymers are preferred, particularly for conjugates prepared using periodate. Length of homopolymeric sequences is related to the desired degree of flexibility of the linkage. Preferably, the homopolymeric segment is absent or comprises from about 1 to about 20 residues in length, more preferably 6 to 15 residues and even more preferably 6 to 12 residues in length.

Complementary sequences are preferred having a G-C content of from about 20 to about 90 percent of the complementary sequence, more preferably from about 40 to 80 percent G-C. Also preferred are complementary sequences that lack appreciable amounts of self-complementarity. Also preferred are complementary sequences comprising a restriction enzyme site, a DNA modifying enzyme site or an RNA modifying enzyme site. Preferably the complementary sequence comprises 10 to 30 basepairs, more preferably 15 to 20 basepairs.

In the examples described below, each of two single-stranded nucleic acids is first attached to a protein molecule by a reaction between a dialdehyde residue produced at the 3' end of the oligonucleotide by periodate oxidation of a ribonucleotide residue, and a hydrazine residue artificially introduced to the protein molecule. A conjugate of the invention is then formed in a separate step by allowing annealing and heteroduplex formation along a complementary segment of the two single-stranded oligonucleotides. In preparing the conjugates of the invention, the following features of such conjugates are intended to inform their preparation. Individual nucleic acids and oligonucleotides are attached at the 5' end or the 3' end, and pairs of oligonucleotides used to prepare the conjugates of the invention are covalently attached to proteins or other biologically active molecules at the 5' end or the 3' end or in combination where some are attached by the 5' end and others by the 3' end; this versatility is of particular importance where the biologically active molecule is covalently linked to one or a multiplicity of oligonucleotides. The nucleic acids covalently linked to biologically active molecules may comprise ribose or deoxyribose, or other sugar as described above, as well as a non-sugar residue in its backbone, in any combination, the choice being limited only by the covalent conjugation reaction method used to prepare the adducts.

The following Examples are intended to further illustrate certain preferred embodiments of the invention and are not limiting in nature.

Illustrative Example 1

Conjugation of Bovine Serum Albumin with Covalently-linked Complementary Nucleic Acid Bovine serum albumin was conjugated with itself in the form of homodimers via heteroduplex formation between nucleic acids covalently linked to the protein molecules, by covalently linking the protein in two separate and independent reactions with two different nucleic acids, followed by heteroduplex formation.

Bovine serum albumin (BSA) was first substituted with carbohydrazide residues in a proportion of its free carboxyl groups. This conversion was performed in a reaction mixture comprising (concentrations of the final reaction mixture) 5 mg/mL BSA (varying with experiment between 1-10 mg/ml), 0.1M carbohydrazide, 1.0M 1-ethyl-3-dimethylamino propyl carbodiimide (EDC), in a solution adjusted to pH 4.6. The reaction was initiated by adding EDC to the other components, and was allowed to proceed at ambient temperature for one minute before being quenched by the addition of an equal volume of 1M sodium acetate buffer, pH 4.75. Longer reaction times were found to lead to an excessive degree of substitution, increasing the risk of precipitation of multimeric conjugates thereafter; the extent to which this problem occurs varies from protein to protein. In the experiments discussed herein, reaction times of up to 5 minutes have been used with success.

The "quenched" reaction solution was then extensively dialyzed against 0.1M sodium acetate buffer, pH 4.6 with stirring and with several changes of dialysis solution. It is particularly important to reduce the free carbohydrazide concentration to negligible levels, since it would otherwise react with nucleic acid dialdehyde in a later step in the reaction sequence.

An oligonucleotide (designated "A" herein) was synthesized using the methods well known in the art, and was prepared having cytosine ribonucleoside at its 3' terminus (the remaining residues in this case being deoxyribonucleotides). The sequence of the "A" oligonucleotide was as follows:
5'-CGCCGGTATGGCCGCAAAAAAAAAA-riboC-3' (SEQ ID No.: 1).
The 15 nucleotides 5' to the oligo A segment of the oligonucleotide was designed to be complementary to the 5' extent of the "B" primer, as described below.

An aqueous solution of 150 µL was prepared containing 30 nmol oligonucleotide A, 48 nmol sodium periodate and 0.1M sodium acetate buffer, pH 4.6, and this mixture allowed to incubate for one hour at ambient temperature. Subsequent experiments suggested that a much shorter period of incubation may suffice and may be preferred, and also that an equimolar amount of periodate, or a bare excess, is preferable.

An aliquot of the above mixture was then mixed with the derivatized, dialyzed bovine serum albumin, in a ratio of 40 nmol of protein (in 1 mL) to 10 nmol of periodate-oxidized oligonucleotide (comprising a nucleic acid dialdehyde), and the mixture again incubated at ambient temperature overnight. The next day the reaction mixture was dialyzed against Tris-buffered saline (20 mM Tris-HCl, pH 7.6, 0.5M NaCl) preparatory to chromatography.

The nucleic acid-protein adduct was separated from remaining protein by passing the dialyzed reaction mixture over an oligo(dT) cellulose column, having a bed volume of 0.5 mL and equilibrated with 20 mM Tris-HCl, pH 7.6, 0.5M NaCl at 4° C. The column was washed with several column volumes to clear unannealed components of the reaction mixture, and then the column was warmed to 37° C. BSA covalently linked to oligonucleotide A and bound to the column through annealing of the oligo A portion of the oligonucleotide was eluted at 37° C. with a solution of 20 mM Tris-HCl, pH 7.6. The product may be repeatedly bound to and eluted from oligo(dT) cellulose under the conditions outlined above to ensure its purity, and was identified by the ratio of spectrophotometric absorbance at 258 nm to that at 280 nm. Results of representative experiments suggested an average content of 1.5 mol nucleic acid bound per mol protein. As it was recognized that unreacted nucleic acid also appears in this fraction, the protein-nucleic acid adduct was further purified by passing the oligo(dT) column eluate over a Sephadex G25 column equilibrated with 20 mM Tris-HCl, pH 7.6.

A similar preparation was made with oligonucleotide B, the sequence of which is shown below and which comprised a cytosine ribonucleoside as the 3' residue. The sequence of the B oligonucleotide was as follows:
5'-GCGGCCATACCGGCGAAAAAAAAAA-riboC-3' (SEQ ID No.:2).
Covalent adducts of oligonucleotide B and BSA protein were prepared essentially as described for oligonucleotide A above.

The conjugate was prepared by mixing equimolar amounts of the two nucleic acid-protein adducts and adding sodium chloride added to a final concentration of 0.5M. Formation of the combined molecule, consisting of two bovine serum albumin molecules linked by the twin nucleic acid chains, was verified by electrophoresis in 10% polyacrylamide gel, in a running buffer of 0.375M Tris-HCl, in the absence of both a "stacking gel" and sodium dodecyl sulphate, in comparison with standards containing modified and unmodified bovine serum albumin.

Illustrative Example 2

Conjugation of F(ab') Fragments with Covalently-linked Complementary Nucleic Acid Antisera were prepared in rabbits against dinitrophenyl (DNP) and dansyl (DNS) haptens, the IgG fraction of the serum proteins isolated, and $F(ab')_2$ fragments prepared, all by methods well known in the art. Then Fab' fragments were prepared and the sulfhydryl groups modified to leave carboxyl groups exposed, as follows. A quantity of $F(ab')_2$ solution in 0.15M sodium chloride buffered to pH 7.0 with 10 mM phosphate buffer, containing about 4 mg protein, was concentrated to about 0.6 mL by centrifugal ultrafiltration; 2-mercaptoethanol (1 µL) was added, the solution mixed and left at 30° C. for 30 minutes. To this reaction mixture was then added 14 mg iodoacetic acid in 0.1 mL water, the solution mixed and again left at 30° C. for 20 minutes. After the reaction was complete, the mixture was dialyzed at 4° C. against four, 1 L changes of 0.15M sodium chloride.

Carbohydrazide derivatives of the resulting F(ab') fragments were then prepared by the method described in Example 1, and exhaustively dialyzed against seven, 1-2 L changes of 0.15M sodium chloride. The dialysate was then concentrated to about 0.55 mL by centrifugal ultrafiltration.

An adduct of the anti-DNS Fab' fragment with the oligonucleotide of sequence A above was then prepared. 40 µL of the nucleic acid solution, containing 10 nanomoles, was mixed with 4 microliters of 4M sodium acetate buffer (pH 4.7) and 2 µL of 10 mM sodium metaperiodate (equivalent to 20 nanomoles). The solution was allowed to stand for 5 minutes at room temperature, and then 0.3 mL of anti-DNS Fab'-carbohydrazide derivative containing 1.9 mg protein (approximately 38 nanomoles) was added. This solution was allowed to stand overnight at 4° C. A considerable excess of protein was used to minimize the formation of adducts containing two nucleic acid chains; additionally, a 2-fold excess of periodate over nucleic acid was used, which is likely to be unnecessary; a slight excess of periodate to nucleic acid has been found to be sufficient. Similarly, a reaction time of 5 minutes as used herein was also in excess, but it was believed to be important to avoid the presence of unoxidized nucleic acid in the conjugation mixture, as described below.

An adduct of the anti-DNP Fab' fragment with the oligonucleotide of sequence B above was prepared essentially as described, though on a half-scale (molar basis).

A hybrid Fab'1 . . . Fab'2 was prepared by mixing volumes of the adduct solutions containing equimolar amounts of the two adducts (4.5 nanomoles each) and allowing the mixture to stand overnight at 4° C. The product was isolated by adsorption chromatography on oligo(dT) cellulose as described in Example 1 and by molecular exclusion Fast Protein Liquid Chromatography (FPLC) on a Superose-12 column equilibrated with 0.15M sodium chloride. These procedures were applied in either order, reproducibly, with full recovery, and the product showed the following additional properties:
Absorbance ratio (260 nm/280 nm): 1.43 to 1.48 (@ approx. 20° C.)
Apparent elution volume on Superose 12: 0.45 column volumes.
(In contrast, the apparent elution volumes of the free Fab' and the free nucleic acid were in the region of 0.56 to 0.58 column volumes and F(ab')$_2$ eluted at 0.52 column volumes). These results were expected on the basis of earlier experiments, wherein the Fab' . . . DNA adduct was found to give a widely spread elution pattern, frequently displaying two recognizable peaks at around 0.50 and 0.56 column volumes, as well as more variable absorbance ratios. These features are believed to be attributable to reversible, less specific, intra- and inter-molecular interactions. Furthermore, conventional gel electrophoretic analysis of the Fab' . . . DNA adduct preparations resulted in apparent partial dissociation of the adduct, reasonably due to heating the adduct preparation at 100° C. in sample buffer.

It should be understood that the foregoing disclosure emphasizes certain specific embodiments of the invention and that all modifications or alternatives equivalent thereto are within the spirit and scope of the invention as set forth in the appended claims.

I claim:

1. A conjugate molecule comprising a multiplicity of proteins, wherein at least a first and second proteins are linked to each other by a flexible nucleic acid linker that is flexible due to the flexibility of single stranded nucleic acid such that the first and second proteins can bind to nonoverlapping epitopes on a desirable analyte and wherein the linker is formed by two nucleic acid single chains of which the first is covalently linked to the first protein and the second is covalently linked to the second protein, and wherein the nucleic acid single chains form a double-stranded heteroduplex of from 10 to 30 base-pairs in length, and wherein at least one of the first and second single stranded nucleic acids has a segment comprising from 6 to 20 consecutive nucleotides that remain free of any base-pairing interaction, and connects the covalent link to the corresponding protein to the heteroduplex.

2. The conjugate molecule of claim 1, wherein first and second nucleic acid single chains are covalently linked to corresponding proteins both by the 3' end or both by the 5' end, or one by the 3' end and one by the 5' end.

3. The conjugate molecule of claim 1, wherein the first and second proteins are the same or different.

4. A conjugate molecule comprising a multiplicity of proteins wherein at least a first and a second protein are linked to each other by a flexible nucleic acid linker that is flexible due to the flexibility of single-stranded nucleic acid such that the first and second proteins can bind to nonoverlapping epitopes on a desirable analyte and wherein the linker is formed of two nucleic acid single chains of which the first is covalently linked to the first protein and the second is covalently linked to the second protein, and wherein the first and second nucleic acid single chains each form double-stranded heteroduplexes of from 10 to 30 base pairs in length with a third nucleic acid and wherein at least one of the first or second nucleic acid single chains has a segment comprised of from 6 to 20 consecutive nucleotides that remain free from any base-pairing interaction and connects the covalent link to the corresponding protein to the segment of the same nucleic acid single chain that forms a heteroduplex with the third nucleic acid, and wherein the third nucleic acid may be a nucleic acid

SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: CHEMICALLY SYNTHESIZED

<400> SEQUENCE: 1
cgccggtatg gccgcaaaaa aaaaac                                           26

<210> SEQ ID NO 2
<211> LENGTH: 26
<212> TYPE: DNA
<213> ORGANISM: Artificial
<220> FEATURE:
<223> OTHER INFORMATION: CHEMICALLY SYNTHESIZED

<400> SEQUENCE: 2
gcggccatac cggcgaaaaa aaaaac                                           26 single chain or a concatenate of nucleic acid chains and wherein the third nucleic acid is not covalently bound to either the first or the second protein.

5. The conjugate molecule of claim 4, wherein the first and second nucleic acid single chains are covalently linked to corresponding proteins both by the 3' end or both by the 5' end, or one by the 3' end and one by the 5' end.

6. The conjugate molecule of claim 4, wherein the first and second proteins are the same or different.

* * * * *